United States Patent [19]
Langdon et al.

[11] Patent Number: 5,368,909
[45] Date of Patent: Nov. 29, 1994

[54] FLUID-PERVIOUS PLASTIC WEB HAVING IMPROVED FLUID DRAINAGE

[75] Inventors: Fred M. Langdon, Cincinnati; John B. Burchnall, West Chester; Gregory B. Hyde, Fairfield, all of Ohio

[73] Assignee: The Procter & Gamble Company, Cincinnati, Ohio

[21] Appl. No.: 42,364

[22] Filed: Apr. 2, 1993

[51] Int. Cl.⁵ .................................. B32B 3/10
[52] U.S. Cl. ........................... 428/137; 428/131; 428/284; 428/286; 428/299; 428/913
[58] Field of Search ............ 428/284, 286, 131, 137, 428/299, 300, 913

[56] References Cited

U.S. PATENT DOCUMENTS

| | | | |
|---|---|---|---|
| 3,043,738 | 7/1962 | Demeter et al. | 156/229 |
| 3,077,882 | 2/1963 | Trewella | 128/156 |
| 3,081,515 | 3/1963 | Griswold et al. | 28/78 |
| 3,165,432 | 1/1965 | Plaskett | 156/244 |
| 3,190,781 | 6/1965 | Metz, Jr. | 156/244 |
| 3,331,728 | 7/1967 | Lane | 161/112 |
| 3,421,964 | 1/1969 | Arbit | 156/244 |
| 3,523,149 | 8/1970 | Hartmann | 264/90 |
| 3,878,014 | 4/1975 | Melead | 156/167 |
| 3,929,135 | 12/1975 | Thompson | 128/287 |
| 3,945,386 | 3/1976 | Anczurowski et al. | 128/287 |
| 3,965,906 | 6/1976 | Karami | 128/287 |
| 3,967,623 | 7/1976 | Butterworth et al. | 128/287 |
| 3,987,792 | 10/1976 | Hernandez et al. | 128/284 |
| 3,994,299 | 11/1976 | Karami | 128/287 |
| 4,077,410 | 3/1978 | Butterworth et al. | 128/287 |
| 4,323,069 | 4/1982 | Ahr et al. | 128/287 |
| 4,342,314 | 8/1982 | Radel et al. | 128/287 |
| 4,609,518 | 9/1986 | Curro et al. | 264/504 |
| 4,619,724 | 10/1986 | Chatow | 156/72 |
| 4,695,422 | 9/1987 | Curro et al. | 264/504 |
| 4,726,976 | 2/1988 | Karami et al. | 428/137 |
| 4,781,962 | 11/1988 | Zamarripa et al. | 428/138 |
| 4,995,930 | 2/1991 | Merz et al. | 156/209 |
| 5,171,238 | 12/1992 | Kajander | 604/383 |
| 5,173,351 | 12/1992 | Ruppel et al. | 428/1.74 |

FOREIGN PATENT DOCUMENTS

| | | | |
|---|---|---|---|
| 0040084 | 11/1981 | European Pat. Off. | A61F 13/00 |
| 0545423A1 | 6/1993 | European Pat. Off. | A61F 13/15 |
| WO93/09741 | 5/1993 | WIPO | A61F 13/15 |
| WO93/22995 | 11/1993 | WIPO | A61F 13/15 |

*Primary Examiner*—James J. Bell
*Attorney, Agent, or Firm*—Kevin C. Johnson; E. K. Linman

[57] ABSTRACT

The present invention provides a resilient, fluid-pervious, laminate, plastic web suitable for use as a topsheet on absorbent articles, especially catamenial articles. The web includes a first layer of polymeric material, a second layer of polymeric material and an intermediate layer of fibrous material. The fibrous material of the intermediate layer extends below the second surface of the web, preferably into the absorbent core. In-use, fluid deposited on the topsheet drains or empties more readily as the fibrous material of the intermediate layer breaks up the fluid meniscuses which form along the second surface of the web, thereby providing improved dryness and cleanliness for the user.

20 Claims, 7 Drawing Sheets

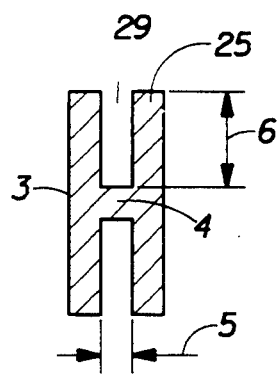
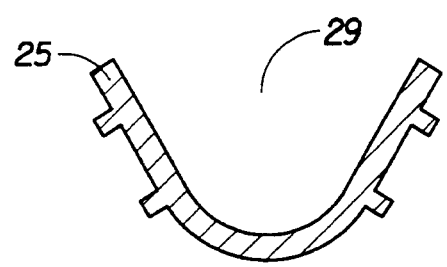
Fig. 5          Fig. 6
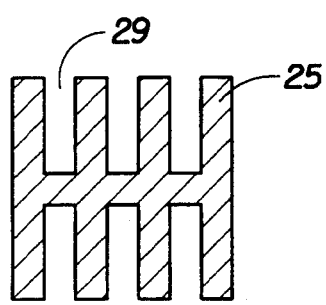
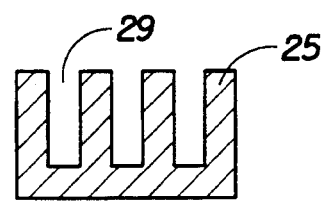
Fig. 7          Fig. 8
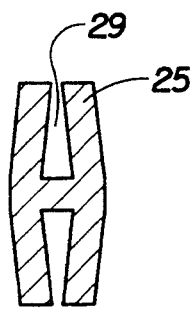 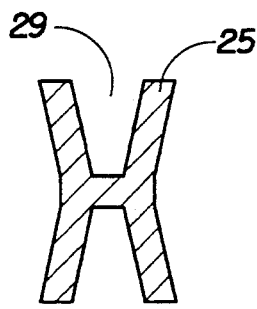 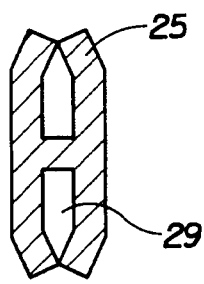
Fig. 9A          Fig. 9B          Fig. 9C

FLUID-PERVIOUS PLASTIC WEB HAVING IMPROVED FLUID DRAINAGE

TECHNICAL FIELD

The present invention relates to resilient, fluid-pervious, plastic webs for use as topsheets on absorbent articles, especially catamenial articles, and more particularly, to such webs having improved fluid drainage, thereby providing improved dryness and cleanliness to the wearer.

BACKGROUND OF THE INVENTION

It has long been known in the disposable absorbent bandage art that it is extremely desirable to construct absorptive devises such as disposable diapers, catamenials, sanitary napkins, incontinent articles, and the like, presenting a dry surface feel to the user to improve wearing comfort and to minimize the development of undesirable skin conditions due to prolonged exposure to moisture absorbed within the bandage.

One viable prior art solution to the aforementioned problem is disclosed in commonly assigned U.S. Pat. No. 4,342,314 issued Radel et al. on Aug. 3, 1982 and hereby incorporated herein by reference. Radel et al. discloses an absorbent bandage with a wearer-contacting topsheet comprising a resilient macroscopically expanded, three-dimensional, plastic web exhibiting a combination of fiber-like and plastic properties. In a preferred embodiment, the macroscopically expanded, three-dimensional, plastic web topsheet disclosed in Radel et al. exhibits a fine scale three-dimensional microstructure comprising a regulated continuum of capillary networks originating in and extending from one surface of the web and terminating in the form of apertures in the opposite surface thereof to promote rapid fluid transport. The web's fiber-like appearance is comprised of a continuum of fiber-like elements, the opposed ends of each of the fiber-like elements are interconnected to at least one other of the fiber-like elements.

A typical capillary network in the Radel et al. structure comprises an uppermost capillary opening or aperture formed by a multiplicity of fiber-elements interconnected to one another in the uppermost plane of the web. Each of the fiber-like elements exhibits a substantially uniform U-shaped cross-section along its length. The cross-section of the fiber-like element comprises a base portion located in the wearer-contacting plane and a sidewall portion joined to each edge of the base portion, the sidewall portions extend generally in the direction of the absorbent pad-contacting surface of the web. The sidewall portions which intersect one another are joined to one another intermediate the wearer contacting surface and the absorbent pad contacting surface of the web, thereby forming a capillary network interconnecting the opposed surfaces of the web.

A topsheet of the type generally disclosed by Radel et al. is highly effective in promoting rapid fluid transfer from the first wearer-contacting surface to the second absorbent pad-contacting surface of the topsheet. Accordingly, topsheets of this type have enjoyed widespread commercial success on catamenial pads due to their clean and dry appearance in use when contrasted to conventional nonwoven fibrous topsheets. While the Radel et al. topsheet is highly effective in promoting rapid transfer of bodily fluids from the first wearer-contacting surface to the second absorbent pad-contacting surface, bodily fluids, e.g., menses, may hang up in the apertures along the pad contacting surface unless the apertures are in fluid transporting contact with an underlying layer, e.g., the absorbent core. Typically, in order to ensure fluid transporting contact between the apertures in the pad-contacting surface and the underlying layers, an adhesive has been used. However, adhesives have a tendency to clog the apertures if applied too heavily. If the apertures become clogged, fluid is not permitted to drain through the topsheet thereby exposing the skin to moisture. In addition, bonding layers together with an adhesive to ensure fluid transporting contact throughout can produce a stiff structure which is uncomfortable. Furthermore, adhesives may not provide sufficient contact between the topsheet and the underlying layers if applied too sparingly or may delaminate and be rendered useless when wetted with body exudate.

SUMMARY OF THE INVENTION

The present invention pertains, in a preferred embodiment, to a resilient, fluid pervious, laminate web suitable for use as a topsheet on absorbent articles, e.g., sanitary napkins, pantiliners, diapers, adult incontinent garments, bandages, and the like. Preferably, the absorbent article includes a backsheet and an absorbent core positioned between the topsheet and the backsheet. The laminate web has a first surface and a second surface remote from the first surface. The web includes a first layer of polymeric material and a second layer of polymeric material secured to the first layer of polymeric material. In a preferred embodiment, the first and second polymeric materials comprise coextruded material. An intermediate layer of fibrous material is positioned between the first layer and the second layer to form a laminate structure. The fibrous material extends below the second surface of the web. Preferably, the fibrous material of the intermediate layer extends into the absorbent core. A plurality of capillaries extend from the first surface to the second surface of the web to transmit fluid through the web.

In a preferred embodiment, the laminate web is a planar two-dimensional structure. In a particularly preferred embodiment, the web is a macroscopically expanded, three-dimensional structure.

In a preferred embodiment, the first layer includes a multiplicity of capillaries being substantially smaller in cross-section than the capillaries extending from the first surface to the second surface. In a particularly preferred embodiment, the first layer includes a plurality of volcano-like microapertures.

In a preferred embodiment the fibrous material comprises synthetic fibers, such as nylon, polyethylene, polypropylene, polyester; bicomponent binder fibers; natural fibers such as cellulosic fibers. Preferably the fibers can have various shapes such as capillary channel fibers and round cross-section fibers.

BRIEF DESCRIPTION OF THE DRAWINGS

While the specification concludes with claims particularly pointing out and distinctly claiming the present invention, it is believed that the present invention will be better understood from the following description in conjunction with the accompanying drawings, in which like reference numbers identify identical elements and wherein;

FIG. 5 is a cross-sectional view of a symmetrical "H"-shaped capillary channel fiber with a planar base (4), width between walls (5), and depth-of-walls (6);

FIG. 6 is a cross-sectional view of a "C"-shaped capillary channel fiber having stabilizing legs depending therefrom;

FIG. 7 is a cross-sectional view of a multiple "H"-shaped capillary fiber;

FIG. 8 is a cross-sectional view of a multiple "U"-shaped capillary channel fiber;

FIG. 9A is a cross-sectional view of an H-shaped capillary channel fiber in a partially collapsed state;

FIG. 9B is a cross-sectional view of an expanded capillary channel fiber;

FIG. 9C is a cross-sectional view of a wholly collapsed capillary channel fiber;

DETAILED DESCRIPTION OF THE INVENTION

1. General Description of the Absorbent Article

As used herein, the term "absorbent article" refers to devices which absorb and contain body exudates, and, more specifically, refers to devices which are placed against or in proximity to the body of the wearer to absorb and contain the various exudates discharged from the body. The term "absorbent article" is intended to include diapers, catamenial pads, sanitary napkins, pantiliners, incontinent pads, and the like. The term "disposable" is used herein to describe absorbent articles which are not intended to be laundered or otherwise restored or reused as an absorbent article (i.e., they are intended to be discarded after a single use, and, preferably, to be recycled, composted or otherwise disposed of in an environmentally compatible manner). A "unitary" absorbent article refers to absorbent articles which are formed of separate parts united together to form a coordinated entity so that they do not require separate manipulative parts like a separate holder and pad.

Figure 1:
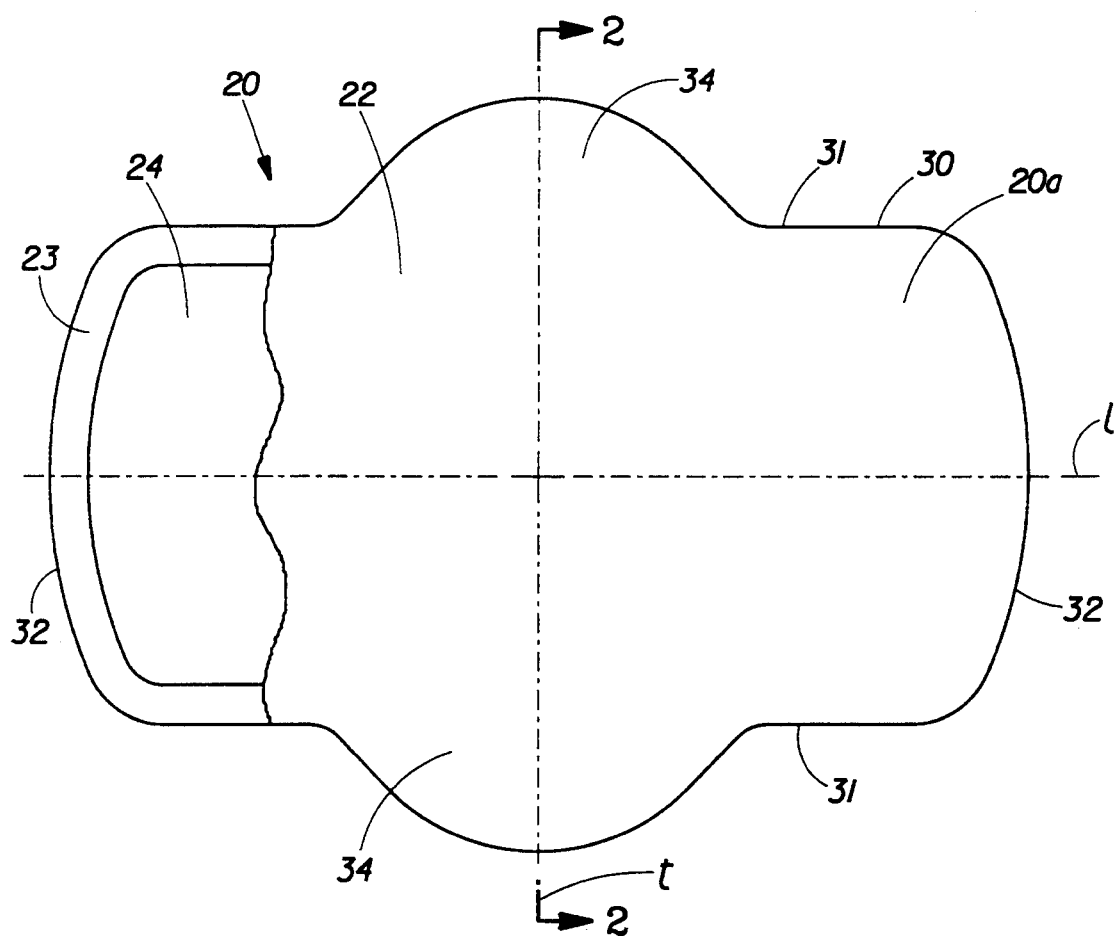
FIG. 1 is a top plan view of a sanitary napkin with portions cut-away to more clearly show the construction of the sanitary napkin.

A preferred embodiment of a unitary disposable absorbent article is the catamenial pad, sanitary napkin 20, shown in FIG. 1. As used herein, the term "sanitary napkin" refers to an absorbent article which is worn by females adjacent to the pudendal region, generally external to the urogenital region, and which is intended to absorb and contain menstrual fluids and other vaginal discharges from the wearer's body (e.g., blood, menses, and urine). Interlabial devices which reside partially within and partially external of the wearer's vestibule are also within the scope of this invention. As used herein, the term "pudendal" refers to the externally visible female genitalia. It should be understood, however, that the present invention is also applicable to other feminine hygiene or catamenial pads such as pantiliners, or other absorbent articles such as incontinence pads, and the like.

The sanitary napkin 20 has two surfaces, a wearer-contacting surface or body-contacting surface or "body surface" 20a and a garment surface 20b. The sanitary napkin 20 is shown in FIG. 1 as viewed from its body surface 20a. The body surface 20a is intended to be worn adjacent to the body of the wearer. The garment surface 20b of the sanitary napkin 20 (shown in FIG. 2) is on the opposite side and is intended to be placed adjacent to the wearer's undergarments when the sanitary napkin 20 is worn.

The sanitary napkin 20 has two centerlines, a longitudinal centerline "l" and a transverse centerline "t". The term "longitudinal", as used herein, refers to a line, axis or direction in the plane of the sanitary napkin 20 that is generally aligned with (e.g., approximately parallel to) a vertical plane which bisects a standing wearer into left and right body halves when the sanitary napkin 20 is worn. The terms "transverse" or "lateral" as used herein, are interchangeable, and refer to a line, axis or direction which lies within the plane of the sanitary napkin 20 that is generally perpendicular to the longitudinal direction.

FIG. 1 is a top plan view of the sanitary napkin 20 of the present invention in its flat-out state with portions of the structure being cut-away to more clearly show the construction of the sanitary napkin 20 and with the portion of the sanitary napkin 20 which faces or contacts the wearer 20a, oriented towards the viewer. As shown in FIG. 1, the sanitary napkin 20 preferably comprises a liquid pervious topsheet 22, a liquid impervious backsheet 23 joined with the topsheet 22, and an absorbent core 24 positioned between the topsheet 22 and the backsheet 23.

FIG. 1 also shows that the sanitary napkin 20 has a periphery 30 which is defined by the outer edges of the sanitary napkin 20 in which the longitudinal edges (or "side edges") are designated 31 and the end edges (or "ends") are designated 32.

Sanitary napkin 20 preferably includes optional side flaps or "wings" 34 that are folded around the crotch portion of the wearer's panties. The side flaps 34 can serve a number of purposes, including, but not limited to protecting the wearer's panties from soiling and keeping the sanitary napkin secured to the wearer's panties.

Figure 2:
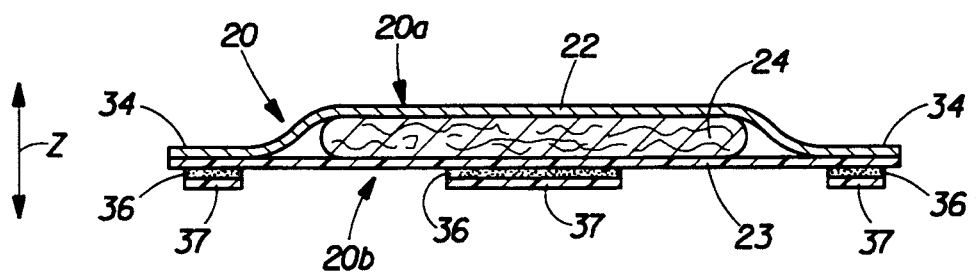
FIG. 2 is a cross-sectional view of the sanitary napkin of FIG. 1 taken along line 2—2.

FIG. 2 is a cross-sectional view of the sanitary napkin 20 taken along section line 2—2 of FIG. 1. As can be seen in FIG. 2 the sanitary napkin 20 preferably includes an adhesive fastening means 36 for attaching the sanitary napkin 20 to the undergarment of the wearer. Removable release liners 37 cover the adhesive fastening means 36 to keep the adhesive from sticking to a surface other than the crotch portion of the undergarment prior to use.

In addition to having a longitudinal direction and a transverse direction, the sanitary napkin 20 also has a "z" direction or axis, which is the direction proceeding down through the topsheet 22 and into whatever fluid storage core 24 that may be provided. The objective is to provide a continuous path between the topsheet 22 and underlying layer or layers of the articles herein, such that fluid is eventually drawn in the "z" direction and away from the topsheet of the article into its ultimate storage layer. In a preferred embodiment the continuous path will have a gradient of increasing capillary attraction which facilitates fluid flow down into the storage medium.

The individual components of the sanitary napkin will now be looked at in greater detail.

2. Individual Components of the Sanitary Napkin

A. The Topsheet

Figure 3:
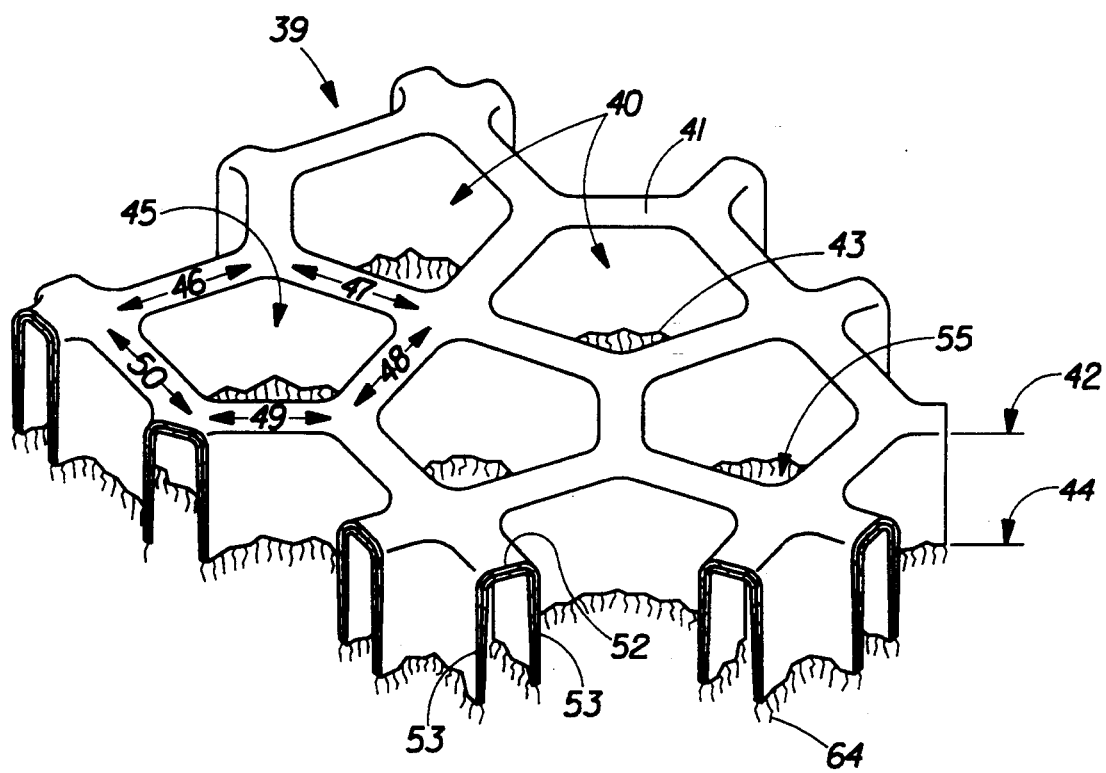
FIG. 3 is an enlarged, partially segmented, perspective illustration of a preferred fluid pervious laminate web of the present invention.

FIG. 3 is an enlarged partially segmented, perspective illustration of a preferred embodiment of a macroscopically expanded, three-dimensional, fiber-like, fluid pervious, laminate, plastic web 39 which has been found suitable for use as a topsheet 22 on sanitary napkin 20. The term "macroscopically expanded", when used to describe three-dimensional plastic webs of the present invention, refers to webs, ribbons and films which have been caused to conform to the surface of a three-dimensional forming structure so that both surfaces thereof exhibit a three-dimensional pattern of surface aberrations corresponding to the macroscopic cross-section of said forming structure, the surface aberrations comprising said pattern being individually discernible to the normal naked eye, i.e., a normal naked eye having 20/20 vision unaided by any instrument that changes the apparent size or distance of an object or otherwise alters the visual powers of the eye, when the perpendicular distance between the viewer's eye and the plane of the web is about 12 inches. The term "fiber-like", as utilized herein to describe the appearance of plastic webs of the present invention, refers generally to any fine scale pattern of apertures, random or nonrandom, reticulated or non-reticulated, which connote an overall appearance and impression of a woven or non-woven fibrous web when viewed by the human eye. As can be seen in FIG. 3, the webs fiber-like appearance is comprised of a continuum of fiber-like elements, the opposed ends of each of the fiber-like elements are interconnected to at least one other of the fiber-like elements. In the embodiment disclosed in FIG. 3, the interconnected fiber-like elements form a pattern network of pentagonally shaped capillaries 40. The web 39, which exhibits a fiber-like appearance, embodies a three-dimensional microstructure extending from the web's uppermost or wearer-contacting surface 41 in plane 42 to its lowermost or absorbent pad contacting surface 43 in plane 44 to promote rapid fluid transport from the uppermost surface 41 to the lowermost surface 43 of the web without lateral transmission of fluid between adjacent capillaries 40. As utilized herein, the term "microstructure" refers to a structure of such fine scale that its precise detail is readily perceived by the human eye only upon magnification by microscopic or other means well known in the art.

Apertures 45 are formed by a multiplicity of intersecting fiber-like elements, e.g., elements 46, 47, 48, 49, and 50, interconnected to one another in the first surface of the web. Each fiber-like element comprises a base portion, e.g., base portion 52, located in plane 42. Each base portion has a sidewall portion, e.g., sidewall portions 53, attached to each edge thereof. The sidewall portions 53 extend generally in the direction of the second surface 43 of the web. The intersecting sidewall portions of the fiber-like elements are interconnected to one another intermediate the first and second surfaces of the web and terminate substantially concurrently with one another in the plane 44 of the second surface.

In a particularly preferred embodiment, the interconnected sidewall portions terminate substantially concurrently with one another in the plane of the second surface 44 to form apertures 55 in the second surface 43 of the web. The network of capillaries 40 formed by the interconnected sidewall portions allows for free transfer of fluids from the first surface of the web directly to the second surface of the web without lateral transmission of the fluid between adjacent capillaries.

Figure 4:
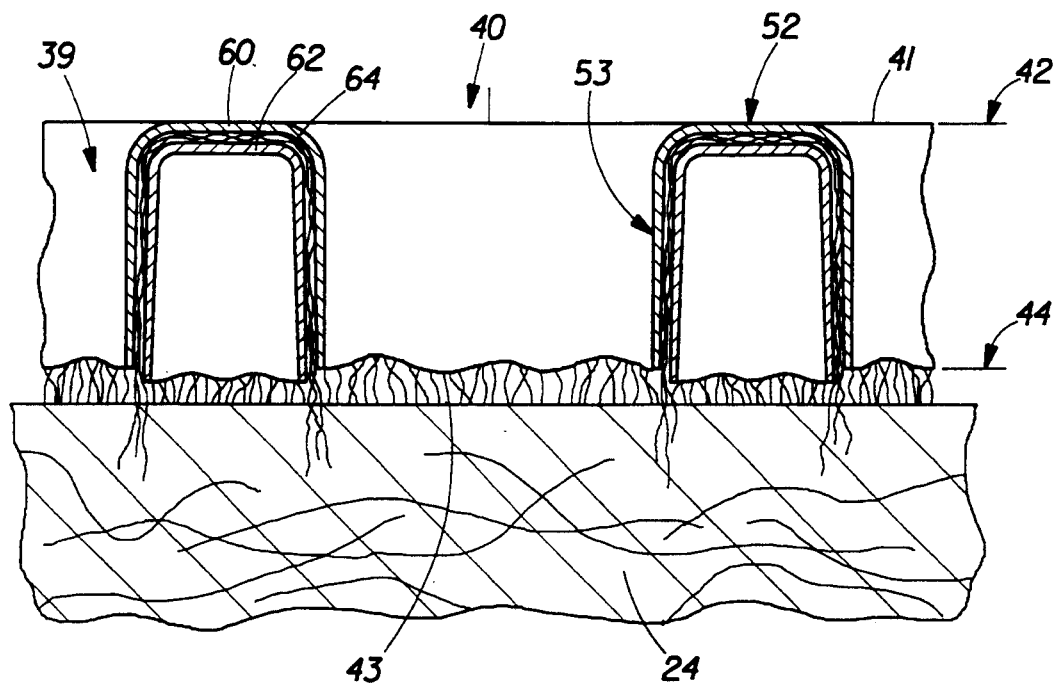
FIG. 4 is an enlarged, segmented, cross-sectional illustration of the fluid pervious laminate web of FIG. 3 and a fluid storage core.

FIG. 4 is an enlarged segmented, cross-sectional illustration of the macroscopically expanded, three-dimensional, fiber-like, fluid pervious plastic web 39 of the present invention. As can be seen in FIG. 4, the web 39 is a laminate comprised of a first, top or uppermost layer 60, a second, bottom or lowermost layer 62 and a intermediate layer 64 sandwiched between uppermost layer 60 and lowermost layer 62.

The uppermost layer 60 and the lowermost layer 62 are preferably formed from thermoplastic materials, e.g., polyethylene, polypropylene, ethylene vinyl acetate (EVA) or any combination of the above materials.

The intermediate layer 64 is preferably comprised of synthetic fibers, such as nylon, polyethylene, polypropylene, polyester, bicomponent binder fibers, or natural fibers, such as cellulosic fibers or any combination of the above. The shape of the fibers can be of any configuration or cross-section such as round, oval, square, rectangular, star, etc., however, preferred fibers are capillary channel fibers.

Capillary channel fibers are fibers having channels formed therein, preferably, on their exterior surfaces. FIGS. 5 to 9C show examples of some types of capillary channel fibers 25 which may be used to form intermediate layer 64. Suitable capillary channel fibers are described below, and in the following Patent Applications which were filed on Jul. 23, 1991: U.S. patent applications Ser. No. 07/734,404 filed in the names of Thompson et al.; U.S. patent application Ser. No. 07/734,392 filed in the names Thompson et al.; and, U.S. patent application Ser. No. 07/734,405 filed in the names of Buenger et al. These patent applications may be referred to collectively as the "Capillary Channel Fiber" patent application. Suitable capillary channel fibers are also described in EPO Patent Application 0 391 814 published Oct. 10, 1990.

While a variety of capillary channel fibers can be used herein, the following description discusses some preferred characteristics of the capillary channel fibers 25 that are incorporated into the intermediate layer 64 of this invention.

The capillary channel fibers 25 used herein can be prepared from any convenient polymer which is substantially nonswelling when wet. Polymers such as polyethylene, polypropylene, polyesters (preferred), and the like, are useful herein, so long as they are spinnable such that they can be formed with external capillary channels, as noted hereinabove. Conveniently, the polymers are melt-extrudable. Typically, the capillary channel fibers herein will be prepared from a synthetic polyethylene terephthalate polymer melt having an inherent viscosity ("IV") of from about 0.6 to about 0.9.

(IV is a term of art and can be determined in well-known fashion. See, for example, U.S. Pat. No. 4,829,761 at column 8.) The IV of a polymer melt bears some relationship to the ability of the polymer to retain the shape of the capillary channel walls, and is related to the average molecular weight of the polymers. For example, it is convenient to employ a polyester having an inherent viscosity of about 0.7 herein, but it would be more preferred to employ a polymer having an inherent viscosity of about 0.9.

The capillary channel fibers 25 preferably have a denier of about 10 to about 22. However, it is to be understood that the denier of the fibers used is within the discretion of the formulator, and the denier per fiber can easily be in the range of about 5 to about 35.

The depth:width ratio of the capillary channels herein is preferably about 2.0, but processing restrictions, as noted above, as well as for economic reasons, a depth:width ratio of about 1.3 is typically employed. Typical and readily producible capillary channel fibers which are quite satisfactory for use herein thus have a depth-of-walls of about 46 microns and a width-between-walls of about 33 microns. The walls, themselves, are typically about 3–15 microns thick. Although variations in these dimensions are acceptable, capillary channel fibers prepared from polyester and having these characteristics are quite effective for their intended purpose. Such fibers can be prepared using conventional operating equipment and readily withstand pressures of the type encountered in sanitary devices, especially sanitary napkins and pantiliners, without collapse or spreading of the capillary channel walls to such an extent that their capillary function is lost.

The capillary channels 29 can be of various shapes. Certain shapes can offer particular advantages in particular product applications. For example, "U"-shaped, "H"-shaped, "C"-shaped with stabilizing legs depending therefrom and "V"-shaped capillary channels 25 may be used. Furthermore, the basic shapes may be repeated (see Figures), or even branched, to produce fibers containing multiple channels, but it will be appreciated that when more than about three repeating shapes are used, some additional stiffness may be noted in the fibers. The multiple "U" fibers of FIG. 6 offer the additional advantages of having additional capillarity due to face-to-face contact and being easily curled.

The manufacture of capillary channel fibers 25 of the type employed herein is described in EPO Application 391,814 and in co-pending U.S. continuation-in-part Application entitled "Fibers Capable of Spontaneously Transporting Fluids", Ser. No. 07/736,261, filed Jul. 23, 1991, Inventors Phillips, Jones et al., Eastman Chemical Company; co-pending U.S. patent application entitled "Spinneret Orifices and Filament Cross-Sections with Stabilizing Legs Therefrom", Ser. No. 07/918,174, filed Jul. 23, 1992, Inventors Phillips, et al.; and in co-pending U.S. patent application entitled "Open Capillary Channel Structures, Improved Process for Making Capillary Channel Structures, and Extrusion Die for Use Therein", Ser. No. 07/482,446, filed Feb. 20, 1990, inventors Thompson and Krautter.

While the polymers used to prepare the capillary channel fibers herein are not, themselves, water-absorbent (nor are they absorbent to urine or blood-containing fluid such as menses), the fibers themselves are most preferably hydrophilic. Since most synthetic polymers are hydrophobic, the capillary channel fibers herein are surface-treated in order to render them hydrophilic.

The surface treatment of polymeric fibers involves processes which are well-known in the extensive fiber literature. In general, such processes involve treating the surface of the fibers with a "hydrophilizing agent", especially a surfactant. (Hydrophilization, which results in wettability of the fibers by aqueous fluids, can routinely be measured, for example, using contact angle measurements. In general, a contact angle less than 90° indicates a hydrophilic surface. A CAHN Surface Force Analyzer (SFA 222) can be used to measure hydrophilicity, as can a variety of other instruments known in the art.) Typical surfactant useful in such processes include various nonionic and anionic detersive surfactants of the general type known in the laundry literature. Hydrophilizing agents include wetting agents such as polyethylene glycol monolaurates (e.g., PEGOSPERSE 200ML, a polyethylene glycol 200 monolaurate available from Lonza, Inc., Williamsport, Pa., USA), and ethoxylated oleyl alcohols (e.g., VOLPO-3, available from Croda, Inc., New York, N.Y., USA). Other types of hydrophilizing agents and techniques can also be used, including those well known to those skilled in the fiber and textile arts for increasing wicking performance, improving soil release properties, etc. Hydrophilizing agents can be added to the polymer at various stages prior to use, though preferably prior to drawing of the capillary channel fibers to their final size. For example, the hydrophilizing agent can be added in advance to the polymer prior to melting or blended into the polymer subsequent to melting. The additive hydrophilizing agent can also be applied to the polymer subsequent to formation, e.g., subsequent to exit from an extrusion die in a melt, wet, or dry spinning process, preferably prior to drawing of the fiber to small diameter. Of course, since the articles herein are intended to come into contact with sensitive regions of the human body, it is preferred that surfactants used to hydrophilize the surfaces of the capillary channel fibers be nontoxic and nonirritating to human skin. Various surfactant treatments for hydrophilizing the capillary channel fibers are described in the Examples hereinafter. Another method for hydrophilizing fibrous surfaces involves subjecting said surfaces to ionizing radiation, e.g., in a plasma, and such methods have the advantage that there is no surfactant residue on the surface of the fibers. Whatever the means, the overall objective is to secure capillary channel fibers for use herein which are spontaneously wettable by the fluids they are intended to transport.

The fibrous material of the intermediate layer 64 may be a nonwoven. The nonwoven is preferably comprised of 0.5 inch helically curled, staple, capillary channel fibers 25. Methods for forming the nonwoven include carding, rando process, spunbond, and the like. Bonding methods may include thermal bonding, needlepunching, hydroentangling, and the like. The fibers have a denier per filament of about 10. The resultant nonwoven preferably has a basis weight of about 0.5 oz/yd². A suitable nonwoven comprised of capillary channel fibers 25 is disclosed in U.S. patent application entitled "Fluid Accepting, Transporting, and Retaining Structure", Ser. No. 07/943,261, filed Sep. 10, 1992, Inventors Thompson et al.

Alternatively, the intermediate layer 64 may comprise nonbonded fibers. Preferably, the nonbonded fibers of intermediate layer 64 are capillary channel fibers 25. In a particularly preferred embodiment, the nonbonded fibers are chopped to a length of about 0.5 inch prior to being blown or deposited between uppermost layer 60 and lowermost layer 62, as will be described in detail below.

As can be seen in FIG. 4 intermediate layer 64 extends below the second surface 43 of web 39 located in lowermost plane 44. Preferably, the intermediate layer 64 of fibrous material is in fluid transporting contact with fluid storage core 24 located immediately adjacent and underneath laminate web 39. In use, bodily fluids will initially impinge the first surface 41 of laminate web 39. Fluid will then move through the capillaries 40 from the first or uppermost surface 41 to the second or lowermost surface 43. As fluid reaches the aperture 55 in the lowermost surface of the web 39 it contacts the fibrous material of intermediate layer 64. The fibers of intermediate layer 64 break the fluid meniscuses which tend to form along the second surface 43 of the web 39 allowing the capillaries 40 to completely drain. By draining the capillaries of bodily fluids the web 39 provides a drier and cleaner topsheet 22. By draining substantially all of the fluid within the network of capillaries 40, the web 39 is essentially renewed for the next infusion of bodily fluids.

In addition to breaking up the fluid meniscuses along the second surface of the web, the fibrous material of intermediate layer 64 may provide better fluid integration with the absorbent core 24 through fiber entanglement of the fibrous material of the absorbent core 24 and the fibrous material of the intermediate layer 64. Fiber entanglement between the fibrous material of the intermediate layer 64 and the absorbent core 24 can be enhanced by the helically curled nature of the fibrous material of the intermediate layer 64.

By improving fluid integration between the topsheet and the underlying absorbent core a more dependable fluid passageway is created as opposed to conventional adhesive or thermal bonding. Conventional adhesives if applied too strongly have a tendency to block the fluid passageways in the capillaries thus preventing the capillaries from properly draining and emptying the bodily fluids into the underlying absorbent core. In addition, excessive use of adhesives tends to create a stiff, rigid absorbent article which is neither comfortable or effective in its use to absorb bodily fluids. Conventional thermal bonding melts together the topsheet and core by partially destroying selected portions of each in the melting or fusing process. These destroyed portions are rendered impervious to the passage of fluid.

By providing a continuous path for bodily fluids between the topsheet and immediate underlying layer, e.g., secondary topsheet or absorbent core, the topsheet is renewed for the next infusion of bodily fluid, thereby leaving the topsheet with a fresh, dry appearance and feel. The sanitary napkin 20 is able to continue to receive fluid until the absorbent core 24 becomes saturated.

As can be seen in FIG. 4 innermost layer 62 may extend further in the z direction than uppermost layer 60. This is due to the fact that as the film is formed over the forming screen the uppermost layer 60 must travel a greater distance than lowermost layer 62. The degree in difference in the extension in the z direction between uppermost layer 60 and lowermost layer 62 may also be affected by the mechanical properties of the film used to form each layer and forming process conditions. As the film properties are varied the exposure to the fibrous material of intermediate layer 64 can be varied accordingly.

The opacity of uppermost layer 60 and lowermost layer 62 may also be changed as desired. For example, uppermost layer 60 may be relatively transparent or clear to provide a more clothlike visual appearance due to the exposure of the fibrous material of intermediate layer 64. The opacity of innermost layer 62 may be increased to provide a masking affect to cover or conceal bodily fluids absorbed within the absorbent core 24 or provide visual contrast so that fibrous material 64 becomes more visible to the user.

The various layers of macroscopically expanded web 39 may also be treated with certain finishes or resins in order to enhance certain fluid properties. Preferably, the uppermost layer 60 has a generally hydrophobic finish as compared with intermediate layer 64 and lowermost layer 62 which are generally preferably more hydrophilic. The fluid which comes into contact with such a structure would then experience a hydrophilicity gradient, thus creating a "driving" force in the direction of the core 24 provided by the surface finishes. This driving force is preferable to one provided by decreased pore size, since flow is directional without any impediment which may be caused by the decreased pore size in the z direction.

Figure 10:
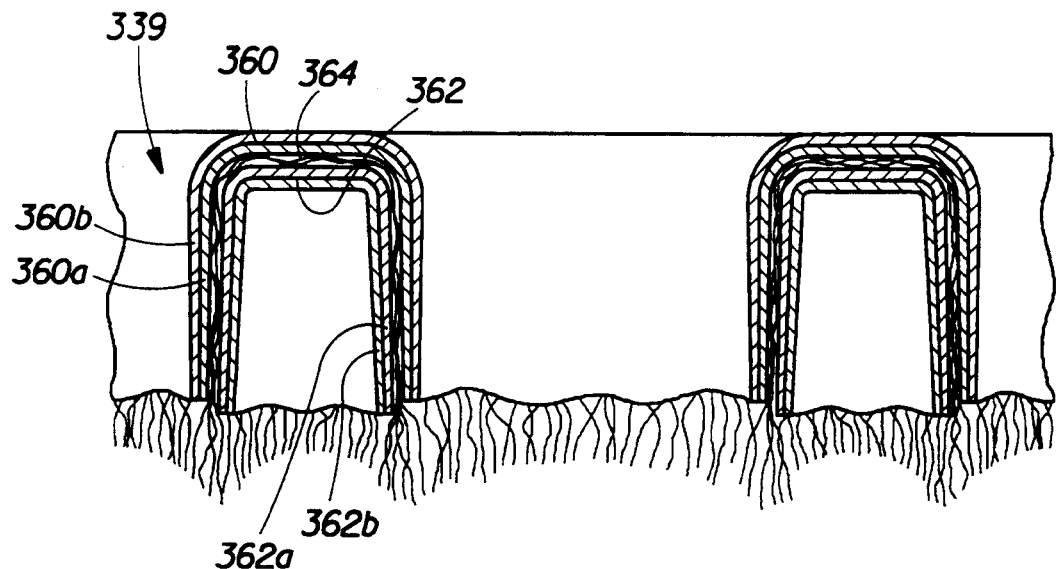
FIG. 10 is an enlarged, segmented, cross-sectional illustration of another preferred embodiment of a fluid pervious laminate web of the present invention.

FIG. 10 is an enlarged, segmented, cross-sectional illustration of another preferred embodiment of a macroscopically expanded, three-dimensional, web 339 suitable for use as a topsheet on an absorbent article. As can be seen in FIG. 10 the web 339 comprises an upper or outermost layer 360, a lower or innermost layer 362 and an intermediate layer 364. Intermediate layer 364 is preferably comprised of a fibrous material as mentioned above. Layers 360 and 362 are each comprised of a coextruded film. Preferably the outermost layer 360 comprises an inner layer 360a and an outer layer 360b. Similarly, innermost layer 362 comprises an inner layer 360a and an outer layer 362b. Preferably, the inner layers, 360a and 362a, are comprised of a polymer having a first melting point temperature which is lower than the melting point temperature of the outermost layers, 360b and 362b. Therefore, when the film is subjected to heat at a temperature above the first melting point temperature of layers 360a and 362a, and below the melting point temperature of the second or outer layers, 360b and 362b, a thermal bond is obtained directly between the outermost layer 360 and innermost layer 362. Preferably the inner layers 360a and 362a are substantially comprised of EVA whereas the outermost layers are substantially comprised of polyethylene.

Alternatively, outermost layer 360 may be comprised of a coextruded film, as shown in FIG. 10, whereas innermost layer 362 is a homogeneous structure as illustrated in FIG. 4. Alternatively outermost layer 360 may be comprised of a homogeneous structure, as illustrated in FIG. 4, and innermost layer 362 may be comprised of a coextruded film as illustrated in FIG. 10. It will be apparent to one skilled in the art that the composition of the various layers of web 339 can be varied depending upon the needs of the manufacturer.

Figure 11:
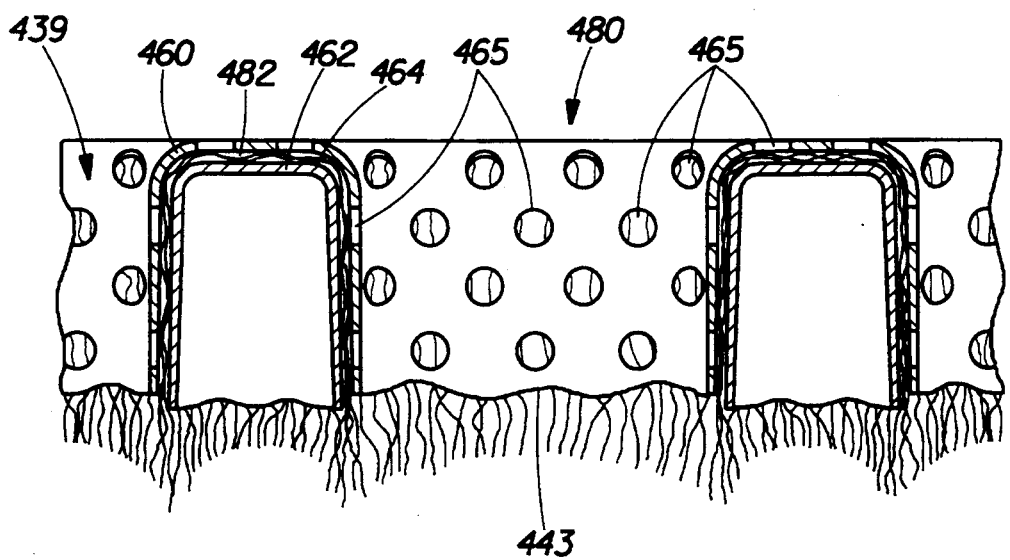
FIG. 11 is an enlarged, segmented, cross-sectional illustration of another preferred embodiment of a fluid pervious laminate web of the present invention.

FIG. 11 is an enlarged, segmented, cross-sectional view of another preferred embodiment of a macroscopically expanded, three-dimensional web 439 suitable for use as a topsheet on an absorbent article. As can be seen in FIG. 11, the web 439 comprises an upper or outermost layer 460, a lower or innermost layer 462 and an intermediate layer 464. Innermost layer 462 is preferably comprised of a homogeneous structure as disclosed in FIG. 4. Intermediate layer 464 is preferably comprised of a fibrous material as disclosed above. The outermost layer 460 of web 439 comprises a plurality of microapertures 465. Preferably the microapertures 465 are a pattern of discrete volcano-like surface aberrations providing a soft and silky tactile impression on the outermost layer 460. The microapertured outer layer is described in greater detail in commonly assigned U.S. Pat. No. 4,629,643 issued to Curro et al. on Dec. 16, 1986 and hereby incorporated herein by reference. The microapertures 465 may also be a plurality of planar apertures. The planar apertures are distinct from the volcano-like surface aberrations in that they do not alter the planar configuration of the film, even on a microscopic scale. The planar apertures penetrate the thickness of the film.

The fibrous material of intermediate layer 464 is in fluid transporting contact with the microapertures 465 in the outermost layer 460 such that any fluid not drained by the capillaries 480 will be drained by the microapertures 465. The fluid will be transported in the interstitial space 482 defined by the three boundaries consisting of the outermost layer 460, innermost layer 462 and the fibrous material of intermediate layer 464. Accordingly, fluid moves from microapertures 465 and through the interstitial space 482 to the second surface 443 of web 439.

Alternatively the outermost layer 460 of web 439 may comprise a multiplicity of fluid-handling capillaries on the first surface of the web which are substantially smaller in cross-section than the network of fluid handling capillaries 40. The smaller fluid handling capillaries exhibit a degree of capillary suction sufficient to transmit static fluid on the first surface of the web generally in the direction of the second surface of the web by capillary attraction. The substantially smaller fluid handling capillaries are described in greater detail in commonly assigned U.S. Pat. No. 4,637,819 issued to Ouellette et al. on Jan. 20, 1987 and hereby incorporated herein by reference.

Figure 12:
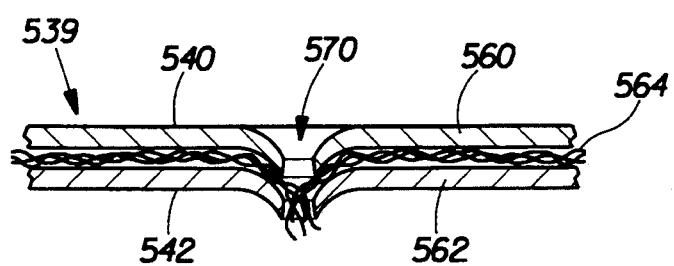
FIG. 12 is an enlarged, segmented, cross-sectional illustration of another preferred embodiment of a fluid pervious laminate web of the present invention.

FIG. 12 is an enlarged, segmented, cross-sectional view of another preferred embodiment of a web 539 suitable for use as a topsheet. The web 539 comprises an upper or outermost layer 560, a lower or innermost layer 562 and an intermediate layer 564. As can be seen from FIG. 12 the web 539 is a "planar" structure having a plurality of apertures 570 therein. As used herein the term "planar", refers to the overall condition of the web when viewed by the normal naked eye on a macroscopic scale. The web 539 has a first surface 540 and a second surface 542. The fibrous material of the intermediate layer 564 extends below the second surface 542 of the web 539. Accordingly, any fluid deposited on the first surface 540 of web 539 will be transmitted through apertures 570 toward the second surface 542. The fibrous material extending below the second surface 542 will break up the fluid meniscuses that tend to form along the second surface 542, thus permitting the apertures 570 to be completely drained of any fluid deposited therein.

B. The Absorbent Core

The absorbent core 24 may be any absorbent means which is capable of absorbing or retaining liquids (e.g., menses and/or urine). As shown in FIGS. 1 and 2, the absorbent core 24 has a body surface, a garment surface, side edges, and end edges. The absorbent core 24 may be manufactured in wide variety of sizes and shapes (e.g., rectangular, oval, hourglass, dog bone, asymmetric, etc.) and from a wide variety of liquid-absorbent materials commonly used in sanitary napkins and other absorbent articles such as comminuted wood pulp which is generally referred to as airfelt. An example of other suitable absorbent materials include creped cellulose wadding; meltblown polymers including coform; chemically stiffened, modified or cross-linked cellulosic fibers; capillary channel fibers; synthetic fibers such as crimped polyester fibers; peat moss; tissue including tissue wraps and tissue laminates; absorbent foams; absorbent sponges; superabsorbent polymers; absorbent gelling materials; or any equivalent material or combinations of materials, or mixtures of these.

The configuration and construction of the absorbent core 24 may also be varied (e.g., the absorbent core may have varying caliper zones (e.g., profiled so as to be thicker in the center), hydrophilic gradients, superabsorbent gradients, or lower density and lower average basis weight acquisition zones; or may comprise one or more layers or structures). The total absorbent capacity of the absorbent core 24 should, however, be compatible with the design loading and the intended use of the sanitary napkin 20. Further, the size and absorbent capacity of the absorbent core 24 may be varied to accommodate different uses such as incontinence pads, pantiliners, regular sanitary napkins, or overnight sanitary napkins.

Exemplary absorbent structures for use as the absorbent core 24 of the present invention are described in U.S. Pat. No. 4,950,264 issued to Osborn on Aug. 21, 1990; U.S. Pat. No. 4,610,678 issued to Weisman et al. on Sep. 9, 1986; U.S. Pat. No. 4,834,735 issued to Alemany et al. on May 30, 1989; U.S. Pat. No. 5,009,653 issued to Osborne on Apr. 23, 1991; and European Patent Application No. 0 198 683, The Procter & Gamble Company, published Oct. 22, 1986 in the name of Duenk et al. Each of these patents are incorporated herein by reference.

Alternatively, the absorbent core 24 may comprise a laminate structure comprised of a layer of superabsorbent polymeric (or absorbent gelling material) and one or more sheets or webs of cross-linked cellulosic fibers. Suitable cross-linked cellulosic fibers for the absorbent core 24 are described in U.S. Pat. No. 4,888,093 issued to Cook et al. on Dec. 19, 1989; U.S. Pat. No. 4,822,543 issued to Dean et al. on Apr. 18, 1989; U.S. Pat. No. 4,889,595 issued to Schoggen et al. on Dec. 26, 1989; and U.S. Pat. No. 4,898,642 issued to Moore et al. on Feb. 6, 1990; U.S. Pat. No. 4,935,022 issued Jun. 19, 1990 to Lash et al.; EPO Patent Application Publication Nos. 0 427 316 A2 and 0 427 317 A2 published in the name of Herron et al. on May 15, 1991; and EPO Patent Application Publication No. 0 429 112 A2 published in the name of Herron et al. on May 29, 1991 incorporated herein by reference.

The laminate may be formed of a sheet of cross-linked cellulosic fibers that wraps the layers of particles of absorbent gelling material. The sheet is wrapped so that it appears as having a "c" configuration when viewed from the end. The wrapped sheet forms an upper layer and a lower layer. In alternative embodiments, the laminate can be formed in many other manners, such as by providing separate webs of cross-linked cellulosic material (or other absorbent material) for the different layers of the absorbent core laminate other than a single sheet, or by providing it with additional layers.

In this type of core, curled, twisted, preferably chemically stiffened and cross-linked, cellulose fibers are refined to provide fibers which can be used in sheet form as the absorbent core. The preparation of suitable curled, chemically stiffened cellulosic fibers from which one can prepare the refined, curled, chemical stiffened cellulosic fibers used in detail in U.S. Pat. Nos. 4,888,903; 4,822,543; 4,889,595; 4,889,597; 4,889,596; and 4,898,642.

The use of such fibers in combination with absorbent gelling materials, and means for manufacturing such combinations, are described in U.S. Pat. No. 4,935,022. Such preparations typically involve the use of aldehydes, such as glutaraldehyde, as crosslinking agents. In addition, polycarboxylic acids can be used as crosslinking agents. It will be appreciated that other means for preparing other crosslinked cellulosic fibers are also known, and such fibers may also be used herein, although the fluid absorbency properties may be suboptimal as compared with the above-mentioned fibers. Reference can be made to the various citations in U.S. Pat. No. 4,898,642 and PCT U.S. 89 01581 for other fiber types. Once in hand, the curled cellulosic fibers are refined to provide the fibers used to prepare the preferred absorbent cores used in the practice of this invention.

C. Backsheet

The backsheet 23 is impervious to liquids (e.g., menses and/or urine) and is preferably manufactured from a thin plastic film, although other flexible liquid impervious materials may also be used. As used herein, the term "flexible" refers to materials which are compliant and will readily conform to the general shape and contours of the human body. The backsheet 23 prevents the exudates absorbed and contained in the absorbent core 24 from wetting articles which contact the sanitary napkin 20 such as pants, pajamas and undergarments. The backsheet 23 may thus comprise a woven or nonwoven material, polymeric films such as thermoplastic films of polyethylene or polypropylene, or composite materials such as a film-coated nonwoven material. Preferably, the backsheet is a polyethylene film having a thickness of from about 0.012 mm (0.5 mil) to about 0.051 mm (2.0 mils). Exemplary polyethylene films are manufactured by Clopay Corporation of Cincinnati, Ohio, under the designation P18-0401 and by Ethyl Corporation, Visqueen Division, of Terre Haute, Ind., under the designation XP-39385. The backsheet 23 is preferably embossed and/or matte finished to provide a more clothlike appearance. Further, the backsheet 23 may permit vapors to escape from the absorbent core 24 (i.e., breathable) while still preventing exudates from passing through the backsheet 23.

D. Optional Retaining Means

In use, the sanitary napkin 20 can be held in place by any support means or attachment means well-known for such purposes. Preferably, the sanitary napkin is placed in the user's undergarment or panty and secured thereto by a fastener such as an adhesive 36. The adhesive 36 provides a means for securing the sanitary napkin 20 in the crotch portion of the panty. Thus, a portion or all of the outer surface of the backsheet 23 is coated with adhesive. Any adhesive or glue used in the art for such purposes can be used for the adhesive herein, with pressure-sensitive adhesives being preferred. Suitable adhesives are Century A-305-IV manufactured by the Century Adhesives Corporation of Columbus, Ohio; and Instant Lock 34-2823 manufactured by the national Starch and Chemical Company of Bridgewater, N.J. Suitable adhesive fasteners are also described in U.S. Pat. No. 4,917,697. Before the sanitary napkin is placed in use, the pressure-sensitive adhesive 36 is typically covered with a removable release liner 37 in order to keep the adhesive 36 from drying out or adhering to a surface other than the crotch portion of the panty prior to use. Suitable release liners 37 are also described in the above-referenced U.S. Pat. No. 4,917,697. Any commercially available release liners commonly used for such purposes can be utilized herein. Non-limiting examples of suitable release liners are BL30MG-A Silox E1/0 and BL30MG-A Silox 4P/0 both of which are manufactured by the Akrosil Corporation of Menasha, Wis. The sanitary napkin 20 of the present invention is used by removing the release liner 37 and thereafter placing the sanitary napkin 20 in a panty so that the adhesive 36 contacts the panty. The adhesive 36 maintains the sanitary napkin in its position within the panty during use.

E. Optional Features

The sanitary napkin 20 may also be provided with two flaps 34, each of which are adjacent to and extend laterally from the side edge of the absorbent core. The flaps 34 are configured to drape over the edges of the wearer's panties in the crotch region so that the flaps 34 are disposed between the edges of the wearer's panties and the thighs.

The flaps 34 serve as least two purposes. First, the flaps 34 help serve to prevent swelling of the wearer's body and parities by menstral fluid, preferably by forming a double wall barrier along the edges of the panties. Second, the flaps 34 are preferably provided with attachment means on their garments surface so that the flaps 34 can be folded back under the panty and attached to garment facing side of the panty. In this way, the flaps 34 serve to keep the sanitary napkin 20 properly positioned in the panty.

The flaps 34 can be constructed of various materials including materials similar to the topsheet, backsheet, tissue, or combinations of these materials. Further, the flaps 34 may be a separate element attached to the main body portion of the napkin or can comprise extensions of the topsheet 22 and the backsheet 23 (i.e., unitary).

A number of sanitary napkins having flaps suitable or adaptable for use with the sanitary napkins of the present invention are disclosed in U.S. Pat. No. 4,687,478 entitled "Shaped Sanitary Napkin with Flaps", issued to Van Tilburg on Aug. 18, 1987; U.S. Pat. No. 4,589,876 entitled "Sanitary Napkin", issued to Van Tilburg on May 20, 1986; and U.S. Pat. No. 4,608,047, entitled "Sanitary Napkin Attachment Means", issued to Meddingly on Aug. 26, 1986.

3. Method of Making

Figure 13:
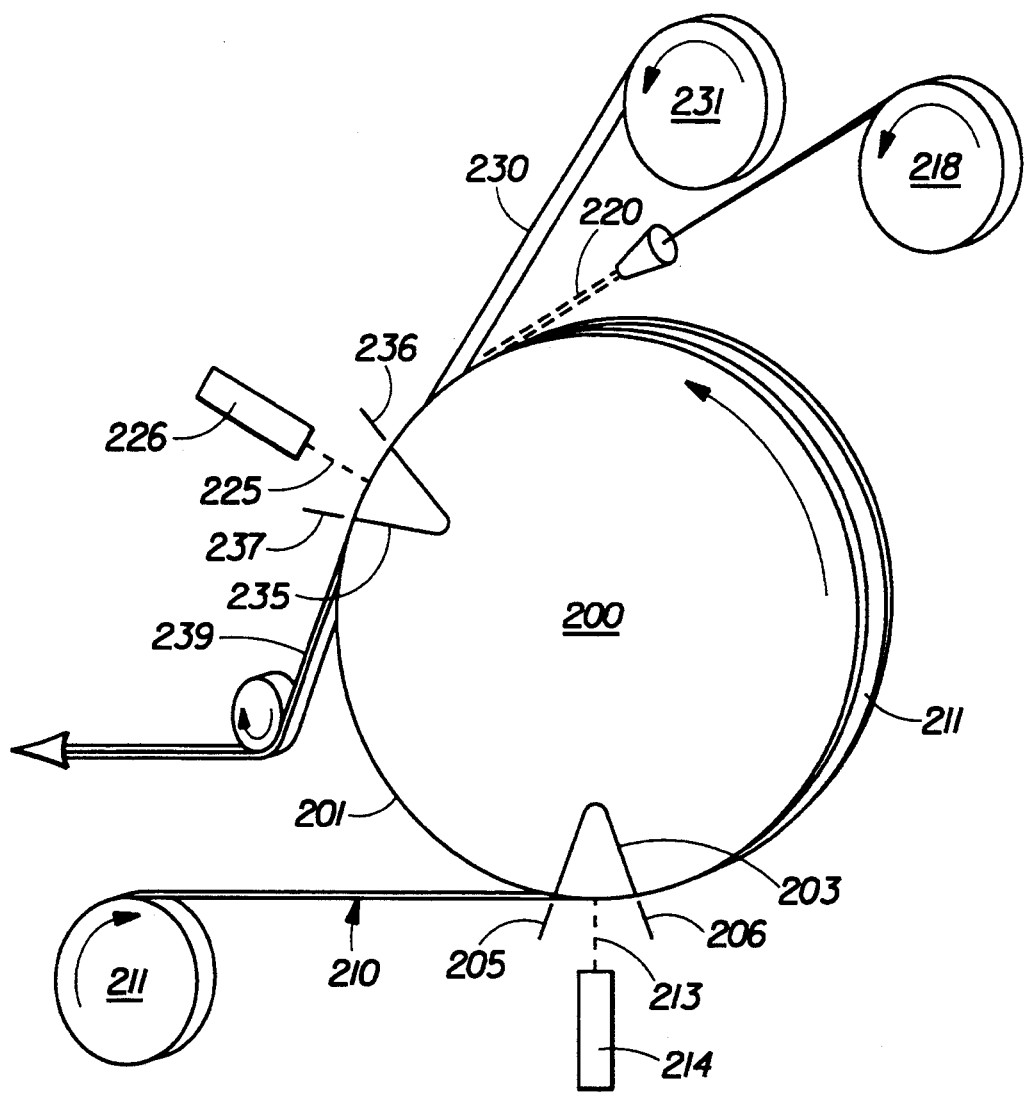
FIG. 13 is a simplified schematic illustration of a preferred process to form the topsheet of the present invention.

FIG. 13 is a simplified, schematic flow diagram of a process for producing fibrous laminated webs of the present invention. A web of substantially planar film 210 comprised of polymeric material such as polyethylene is fed from supply roll 211 onto the surface of forming drum 200 about which a forming structure 201 continuously rotates at substantially the same speed as the incoming web. The web of film 210 is driven by the forming drum 200.

Figure 14:
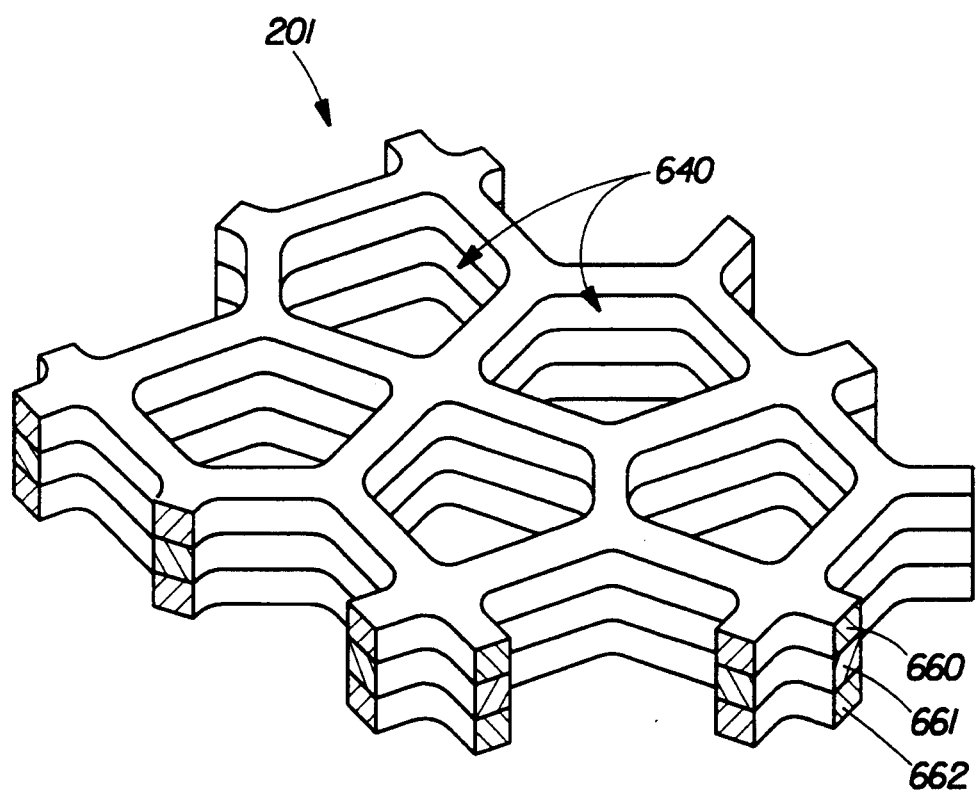
FIG. 14 is a greatly enlarged fragmentary view of the forming structure used to carry out the forming process generally illustrated in FIG. 13.

Forming structure 201, a greatly enlarged fragmentary segment of which is illustrated in FIG. 14, includes a patterned network of pentagonally shaped capillaries 640. The forming structure is preferably construed generally in accordance with the teachings of U.S. Pat. No. 4,342,314 issued to Radel and Thompson on Aug. 3, 1982 which is hereby incorporated by reference herein. Forming structure 201 is comprised of individual lamina 660, 661 and 662. A comparison of the forming structure 201 of FIG. 14 with the web 39 of FIG. 3 reveals the correspondence of the capillaries 40 in web 39 with the capillaries 640 in forming structure 201. The laminate structure is rolled by conventional techniques into a tubular forming structure, as seen in FIG. 13.

The forming drum 200 preferably includes an internally located vacuum chamber 203 which is preferably stationary relative to the moving forming structure 201. A pair of stationary baffles 205, 206 approximately coinciding with the beginning and the end of the vacuum chamber 203 are located adjacent the exterior surface of the forming structure. Intermediate the stationary baffles 205, 206 there is preferably provided means for applying a fluid pressure differential to the substantially planar web of polymeric film 210 as it passes across the suction chamber. In the illustrated embodiment, the fluid pressure differential applicator means comprises a high-pressure liquid nozzle 214 which discharges a Jet of liquid 213, such as water substantially uniformly across the entire width of the web 210. Examples of methods for the production of formed material using a high-pressure liquid stream are disclosed in U.S. Pat. Nos. 4,695,422 issued to Curro et al. on Sep. 22, 1987; 4,778,644 issued to Curro et al. on Oct. 18, 1988; and 4,839,216 issued to Curro et al. on Jun. 13, 1989 all of which are hereby incorporated by reference.

As forming structure 201 rotates, macroscopically expanded, web 211 advances toward fiber blower/chopper 218. As web 211 advances toward fiber blower/chopper 218 it is held on forming structure 201 by tensional forces. Alternatively, web 211 may be held against forming structure 201 as it approaches fiber blower/chopper 218 by a vacuum or other means well known in the art. Fiber blower/chopper 218 deposits loose fibers 220 onto macroscopically expanded, formed film 211 as the forming structure 201 passes fiber blower/chopper 218. Water from liquid nozzle 214 provides the necessary cohesive attraction to hold the fibers 220 on the macroscopically expanded formed film 211 as forming structure 201 rotates. Alternatively, a vacuum could be provided to hold fibers 220 in place between blower/chopper 218 and liquid stream 225 dispersed from nozzle 226. The fibers 220 may also be held against drum 200 by other means known in the art such as additional water, light adhesive, and static forces for example.

A second continuous web of substantially planar film comprised of polymeric material such as polyethylene 230 is fed from supply roll 231 onto the surface structure 201. The web of film 230 is driven by the forming drum 200. The second web 230 is laid directly on the forming structure 201 over the the loose fibers 220 and the first macroscopically expanded, formed film 211. The forming drum 200 preferably includes a second internally located vacuum chamber 235 which is preferably stationary relative to the moving forming structure 201. A pair of stationary baffles 236, 237 approximately coinciding with the beginning and the end of the vacuum chamber 235 are located adjacent the exterior surface of the forming structure. Intermediate the stationary baffles 236, 237 there is preferably provided means for applying a fluid pressure differential to the planar web of polymeric film 230, the fibers 220, and the macroscopically expanded, formed film 211. The fluid pressure differential applicator means comprises a high-pressure liquid nozzle 226 which discharges a jet of liquid 225, such as water, substantially uniformly across the entire width of the materials. The water jet causes the second layer of polymeric material 230 to conform to the forming structure 201. In addition, the fibers 220 are driven down into the forming structure 201 such that they extend beyond the lower or second surface of the now formed laminate web 239. After the laminate web 239 has been formed it is then ready to be introduced as a topsheet on an absorbent article such as a diaper or a sanitary napkin. Alternatively, the laminate web 239 or may be placed on a windup roll for later use.

The fiber blower/chopper 218 may be replaced by a feed roll of nonbonded chopped fibers and a conveyor which transfers the nonbonded chopped fibers and deposits the same on the macroscopically expanded, formed film 211. The fibrous material may be fed to forming structure 201 by any conventional means for feeding fibrous material known in the art.

Alternatively, a nonbonded planar array of chopped fibers may be applied to the forming drum from a moving wire. The chopped fibers may be held against the moving wire by cohesive or static forces. Preferably, the fibers are held against the moving wire by the cohesive forces of water.

In some situations it may be preferable to heat the liquid stream 225 to cause thermal bonding between the uppermost and lowermost layers of the laminate web. In addition, the heated liquid stream 225 may also thermally bond the fibrous material of the intermediate layer to the uppermost and lowermost layers.

Alternatively, an adhesive may be used to secure the uppermost layer to the lowermost layer. The adhesive may be applied in a number of patterns and amounts to create the desired bonding and fluid handling characteristics, described in detail above. The adhesive may be applied onto the macroscopically expanded web 211 prior to the fibrous material 220 being deposited onto said macroscopically expanded web 211. Alternatively, the adhesive may be applied to the polymeric web 230 prior to being fed over fibrous material 220.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A fluid pervious laminate web suitable for use as a topsheet on an absorbent article, said web having a first surface and a second surface, said web comprising:
   (a) a first layer or polymeric film material;
   (b) a second layer of polymeric film material secured to and underlying said first layer of polymeric film material;
   (c) an intermediate layer of fibrous material positioned between said first layer and said second layer forming a laminate structure, said fibrous material extending below said second surface of said web; and
   (d) a plurality of capillaries extending from said first surface to said second surface of said web for the transmission of fluids through said web.

2. The fluid pervious laminate web according to claim 1, wherein said web is a topsheet on an absorbent article, said absorbent article including a backsheet and an absorbent core positioned between said topsheet and said backsheet.

3. The structure according to claim 2, wherein the fibrous material of said intermediate layer is in fluid-transporting contact with said absorbent core.

4. The fluid pervious laminate web according to claim 1, wherein said web is macroscopically expanded.

5. The fluid pervious laminate web according to claim 1, wherein said web is a substantially planar structure.

6. The fluid pervious laminate web according to claim 1, wherein said first layer of polymeric material comprises a coextruded material.

7. The fluid pervious laminate web according to claim 1, wherein said second layer of polymeric film material comprises a coextruded material.

8. The fluid pervious laminate web according to claim 1, wherein said first layer includes a plurality of microapertures.

9. The fluid pervious laminate web according to claim 1, wherein said first layer includes a multiplicity of capillaries, said capillaries being substantially smaller in cross-section than said capillaries extending from said first surface to said second surface of said web.

10. The fluid pervious laminate web according to claim 1, wherein said intermediate layer comprises capillary channel fibers.

11. The fluid pervious laminate web according to claim 1, wherein said intermediate layer is selected from the group consisting of nylon, polyetheylene, polypropylene, polyester, bicomponent binder fibers or cellulosic fibers.

12. A three-dimensional, macroscopically expanded, fluid pervious laminate web suitable for use as a topsheet on an absorbent article, said web having a first surface and a second surface, said web comprising:
 (a) a first layer of polymeric film material;
 (b) a second layer of polymeric film material, secured to and underlying said first layer of polymeric film material;
 (c) an intermediate layer of fibrous material positioned between said first layer and said second layer forming a laminate structure, said fibrous material extending below said second surface of said web; and
 (d) a plurality of capillaries extending from said first surface of said web to said second surface of said web for the transmission of fluids through said web, each of said capillaries originating as an aperture in said first surface of said web and having a continuously interconnected sidewall between said first and said second surfaces, said continuously interconnected sidewall terminating to form an aperture in said second surface.

13. The three-dimensional, macroscopically expanded, fluid pervious laminate web according to claim 12, wherein said web is a topsheet on an absorbent article, said absorbent article including a backsheet and an absorbent core positioned between said topsheet and said backsheet.

14. The structure according to claim 13, wherein the fibrous material of said intermediate layer is in fluid-transporting contact with said absorbent core.

15. The three-dimensional, macroscopically expanded, fluid pervious laminate web according to claim 12, wherein said first layer of polymeric film material comprises a coextruded material.

16. The three-dimensional, macroscopically expanded, fluid pervious laminate web according to claim 12, wherein said second layer of polymeric film material comprises a coextruded material.

17. The three-dimensional, macroscopically expanded, fluid pervious laminate web according to claim 12, wherein said first layer includes a plurality of microapertures.

18. The three-dimensional, macroscopically expanded, fluid pervious laminate web according to claim 12, wherein said first layer includes a multiplicity of capillaries, said capillaries being substantially smaller in cross-section than said capillaries extending from said first surface to said second surface of said web.

19. The three-dimensional, macroscopically expanded, fluid pervious laminate web according to claim 12, wherein said intermediate layer comprises capillary channel fibers.

20. The three-dimensional, macroscopically expanded, fluid pervious laminate web according to claim 12, wherein said intermediate layer is selected from the group consisting of nylon, polyetheylene, polypropylene, polyester, bicomponent binder fibers or cellulosic fibers.

* * * * *